United States Patent [19]

Gussow et al.

[11] Patent Number: 4,558,168
[45] Date of Patent: Dec. 10, 1985

[54] PRODUCTION OF HIGH PURITY BUTENE-1 FROM AN N-BUTANE FEEDSTOCK

[75] Inventors: Stanley Gussow, Macungie; David C. Spence, Coopersburg; William A. Schwartz, Fogelsville, all of Pa.

[73] Assignee: Air Products and Chemicals, Inc., Allentown, Pa.

[21] Appl. No.: 746,605

[22] Filed: Jun. 19, 1985

[51] Int. Cl.[4] .................................................. C07C 7/01
[52] U.S. Cl. .................................... 585/324; 585/314; 585/315; 585/654; 585/655; 585/809; 585/833; 585/836
[58] Field of Search ............... 585/324, 314, 315, 654, 585/655, 809, 833, 836

[56] References Cited

U.S. PATENT DOCUMENTS

| | | | |
|---|---|---|---|
| 2,209,215 | 7/1940 | Wiezerich et al. | 585/315 |
| 2,382,473 | 8/1945 | Frey | 585/315 |
| 2,390,285 | 12/1945 | Zimmerman | 585/315 |
| 2,391,188 | 12/1945 | Patterson | 585/314 |
| 2,395,016 | 2/1946 | Schulze et al. | 585/315 |
| 3,629,478 | 12/1971 | Haunschild | 585/836 |
| 3,671,603 | 6/1972 | Hagemeyer et al. | 585/259 |
| 4,269,668 | 5/1981 | Patel | 585/833 |
| 4,282,389 | 8/1981 | Druste et al. | 585/833 |
| 4,324,924 | 4/1982 | Torck et al. | 585/833 |
| 4,348,260 | 9/1982 | Hokari et al. | 585/833 |
| 4,409,421 | 10/1983 | Herwig et al. | 585/833 |
| 4,434,316 | 2/1984 | Barnette | 585/833 |
| 4,513,153 | 4/1985 | Sandrin | 585/315 |
| 4,523,045 | 6/1985 | Vora | 585/259 |

Primary Examiner—D. E. Gantz
Assistant Examiner—A. Pal
Attorney, Agent, or Firm—Russell L. Brewer; E. Eugene Innis; James C. Simmons

[57] ABSTRACT

This invention relates to a process for producing a high purity butene-1 product from n-butane via a dehydrogenation process. In one embodiment of the process the n-butane is dehydrogenated over a chromia-alumina catalyst and any butadiene formed hydrogenated to monoolefins. The monoolefins are separated and the butene-1 separated from isobutylene by reacting the isobutylene with methanol to form methyl tertiary butyl ether. The methyl tertiary butyl ether is separated from the butene-1 leaving it as a high purity product. Alternatively, the dehydrogenated product from the reactor may be contacted with a solvent to extract butadiene followed by hydrogenation, separation of monoolefins and conversion to methyl tertiary butyl ether.

4 Claims, 3 Drawing Figures

BUTENE-1 FROM N-BUTANE

BUTENE-1 AND BUTADIENE FROM N-BUTANE

PRODUCTION OF HIGH PURITY BUTENE-1 FROM AN N-BUTANE FEEDSTOCK

TECHNICAL FIELD

This invention pertains to a process for producing butene-1 and other hydrocarbons from a feedstock containing n-butane. There is a growing demand for producing butene-1 as a comonomer in the production of linear low density polyethylene. Although many dehydrogenation processes are capable of producing butene-1 from a feedstock containing n-butane, a large portion of the reaction product consists of isobutylene and butene-2 as well as some butadiene. Separation of butene-1 from isobutylene is extremely difficult. Patents would show the production of butadiene as well as processes for separating butene-1 from a C$_4$ cut are as follows:

U.S. Pat. No. 2,209,215 discloses the dehydrogenation of a feedstock containing normal butane in the presence of a chrome oxide on alumina catalyst. Dehydrogenation is typically carried out at temperatures from about 900°–1200° F. The reaction product then is quenched and the butadiene removed by scrubbing, typically with liquid ammonia or ethylene glycol. The remaining butane and butylene fractions then are either polymerized or resubmitted to the dehydrogenation zone for producing additional butadiene.

U.S. Pat. No. 2,382,473 discloses a process for producing butadiene from a feedstock containing n-butane by dehydrogenating normal butane together with recycled C$_4$ hydrocarbons in a single dehydrogenation step to produce butadiene, butene-1 and butene-2 and then separating the reaction products by selective solvent extraction.

U.S. Pat. No. 4,324,924 discloses a process for removing isobutene from a C$_4$ cut by producing methyl tert-butyl ether therefrom. The process described comprises contacting a hydrocarbon C$_4$ cut containing from about 10–60% isobutene with methanol in the presence of an acid catalyst and then fractionating the reaction product obtaining a bottoms consisting essentially of methyl tertiary butyl ether.

U.S. Pat. No. 4,282,389 discloses a process for producing pure methyl tertiary butyl ether and a substantially isbutene-free mixture of C$_4$ hydrocarbons. More particularly, the process discloses contacting a C$_4$ cut containing isobutene and butene-1 with methanol under etherification conditions. The methyl tertiary butyl ether thus formed can then be separated from the butene-1 by fractionation.

SUMMARY OF THE INVENTION

This invention relates to a process for producing butene-1 in high purity from a feedstock containing n-butane. The process involves the dehydrogenation of an n-butane feedstock over a chromia-alumina catalyst to produce a reaction product containing olefinic components. Any butadiene in the reaction product then is hydrogenated to produce the mono olefin. After hydrogenation of butadiene, the reaction product is fractionated forming an overhead predominantly of isobutane, butene-1 and isobutene and a bottoms fraction of n-butane, butene-2, and heavies. The overhead fraction containing butene-1 is reacted with methanol thereby removing isobutene and producing methyl tertiary butyl ether. The reaction product from the ether reaction is separated by fractionation into methyl tertiary butyl ether and a raffinate stream containing butene-1 and isobutane. The raffinate stream is then fractionated to produce high purity butene-1 as a bottoms product.

Another embodiment involves extracting butene-1 and isobutene from the butadiene hydrogenation unit product and then reacting isobutene with methanol to form methyl tertiary butyl ether leaving unreacted butene-1 as a product. Additional butene-1 is produced by isomerization of butene-2 to butene-1.

Another embodiment involves extracting butadiene product upstream of the butadiene hydrogenation unit. After hydrogenation of residual butadiene, the reaction product is fractionated forming an overhead containing isobutane, isobutene, and butene-1 which is then reacted with methanol to form methyl tert butyl ether and a raffinate stream containing isobutane and butene-1. The raffinate stream is then fractionated to produce high purity butene-1 as a bottoms product.

THE DRAWINGS

DETAILED DESCRIPTION OF THE EMBODIMENT

Figure 1:
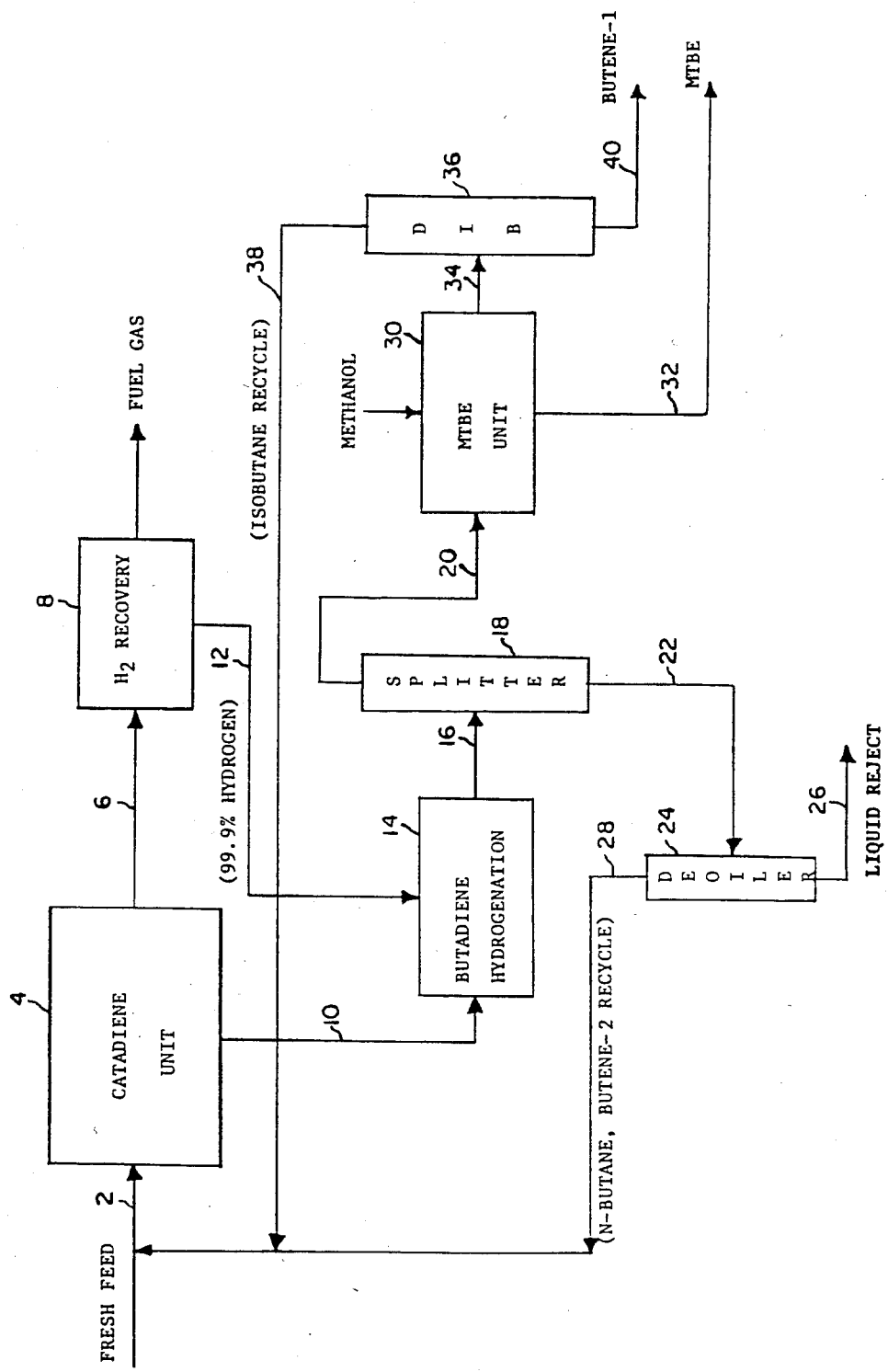
FIG. 1 is a process flow diagram for producing butene-1 from n-butane using butadiene hydrogenation.

To facilitate understanding of the invention, reference is made to the drawing; in particular, FIG. 1. A fresh feed typically consisting of n-butane with minor amounts of C$_{3+}$ components such as propane, isobutane, pentane and higher as obtained from a refinery is passed through line 2 to dehydrogenation unit 4. Typically, the concentration of n-butane will range from about 70% plus by volume with the balance being other hydrocarbon components; e.g. C$_2$ to C$_6$ hydrocarbons. The feedstock is introduced into a dehydrogenation unit 4 containing a chromia-alumina catalyst. An example of a chromia-alumina catalyst utilized for dehydrogenation of butane feedstocks is a CATADIENE catalyst sold by Air Products and Chemicals, Inc. Dehydrogenation of the feedstock is carried out at temperatures from about 900°–1250° F. Chromium oxide levels ranging from about 3 to 40% by weight of the catalyst are common and often these are promoted with alkali metal oxides such as lithium, rubidium, or postassium oxide.

The reaction product from the dehydrogenation unit is recovered with the light gases being removed through line 6 and then through a hydrogen recovery unit 8 for recovering the fuel value therefrom. The major fraction of product from the dehydrogenation unit 4 is then passed to a butadiene hydrogenation unit 14 through line 10 wherein butadiene is contacted with hydrogen under reaction conditions to produce a mixture of isobutane, butane, butene-1, butene-2 and isobutylene.

Hydrogenation is carried out in the presence of a hydrogenation catalyst, typically one containing palladium or platinum as a component. The hydrogen for the hydrogenation is obtained from the hydrogen recovery unit 8 and is transported via line 12 to the butadiene hydrogenation unit 14. The product from the butadiene hydrogenation unit 14 is removed through line 16 to a splitter 18 wherein the reaction product is fractionally separated into an overhead stream consisting primarily of isobutane, butene-1 and isobutylene. Typically, the proportion of butene-1 will range from about 10 to 30% by volume of the total concentration of the overhead. This overhead product is removed from splitter 18 through line 20.

A bottoms fraction is obtained from splitter 18, and this product contains a heavier hydrocarbon fraction consisting of unreacted n-butane, butene-2, and other heavies. This material then is removed from the column through line 22 and sent to a deoiler 24 which produces a liquid reject in line 26 containing $C_5$ plus contaminants originally present in the feedstock. The overhead consisting essentially of butene-2 and n-butene is recycled via line 28 to fresh feed line 2 to the dehydrogenation unit 4. In this way butene-2 is converted to additional butene-1 through isomerization in the dehydrogenation unit thereby increasing butene-1 production.

The overhead from splitter 18 obtained through line 20 then is treated in a unit with methanol under conditions sufficient to effect reaction between the methanol and isobutene. Butene-1 is unreactive with methanol under the reaction conditions and it passes through the ether unit 30 unchanged. Complete reaction of the isobutene in methyl tertiary butyl ether (MTBE) unit 30 is desired since it eliminates the necessity of separating isobutene from butene-1. The overhead from the methyl tertiary butyl ether unit 30 is fractionated in unit 36. An overhead consisting primarily of isobutane is obtained and recycled via line 38 to dehydrogenation unit 4. A bottoms fraction containing a high purity butene-1 is removed via line 40. A purity in excess of 99%/by volume is obtained.

Figure 2:
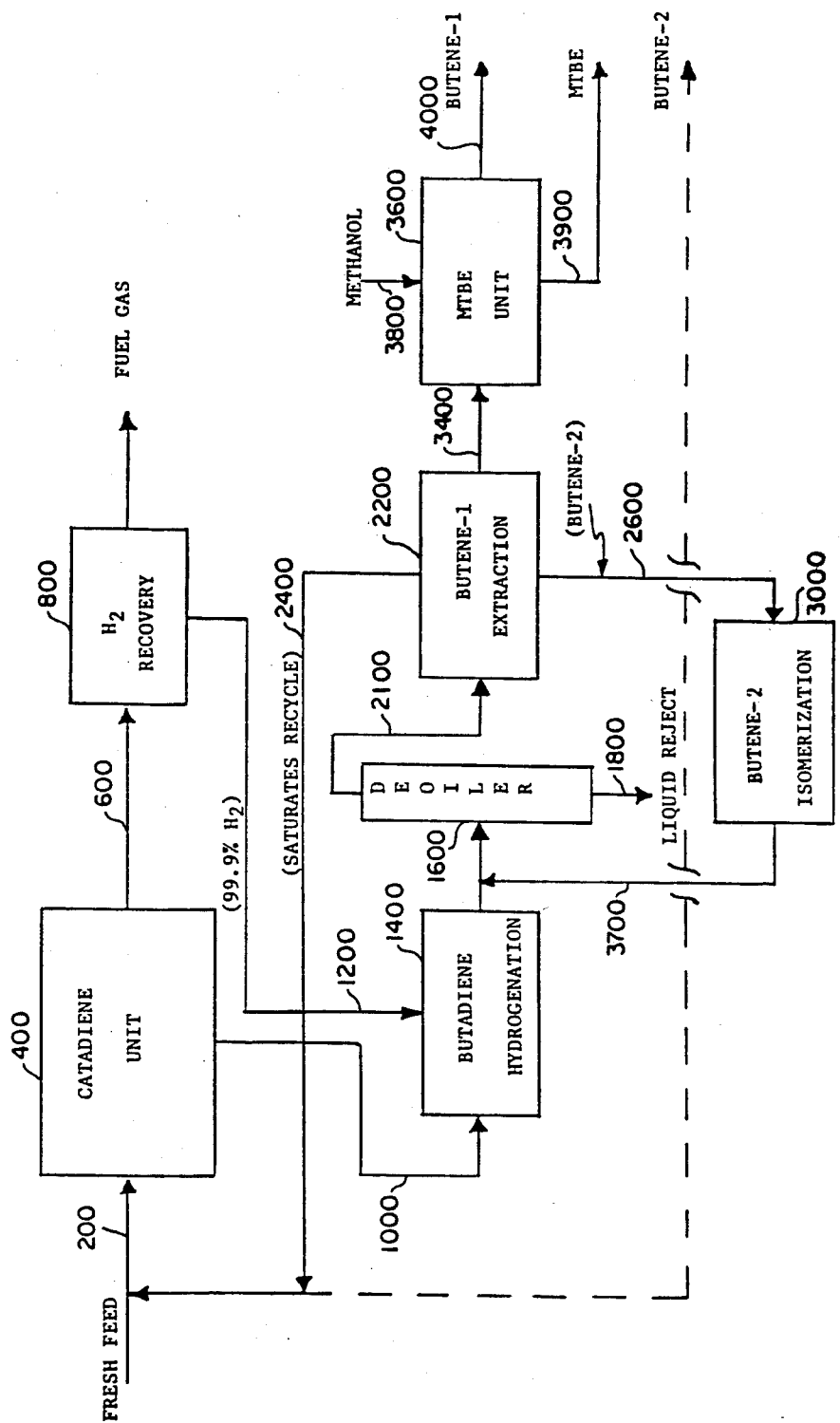
FIG. 2 is a process flow diagram showing production of butene-1 from n-butane employing butene-2 isomerization.

The embodiment shown in FIG. 2 differs slightly from that in FIG. 1 and reference is made to that drawing to facilitate an understanding. As in the process described in FIG. 1 fresh feed containing n-butane is charged through line 200 to a dehydrogenation unit 400 with the lights being removed through line 600 to hydrogen recovery unit 800. The $C_4$ product from the unit is removed through line 1000 from the dehydrogenation unit 400 to a butadiene hydrogenation zone 1400 where butadiene hydrogenation is effected with hydrogen from the hydrogen recovery unit 800. In contrast to the process of FIG. 1 the reaction product from the butadiene hydrogenation unit 1400 is submitted to extractive distillation after first going to a deoiler 1600. The deoiler bottoms stream consisting primarily of $C_{5+}$ hydrocarbons is removed through line 1800 while isobutene, butene-1 and other lights are removed via line 2100 to a butene-1 extraction unit 2200. In the butene-1 extraction the components are contracted with a suitable solvent, e.g. dimethyl formamide, and the iso and normal butenes separated from the saturates. The saturates, consisting primarily of normal butane and isobutane, are recycled through line 2400 back to the dehydrogenation unit 400 via feed line 200. Butene-2 is separated in this extraction zone 2200 producing a bottoms fraction of butene-2 which is removed through line 2600 and isomerized in isomerization unit 3000. Much of the butene-2 is isomerized to butene-1 and the product removed from isomerization unit 3000 through line 3200 and back to deoiler 1600.

The product from the butene-1 extraction unit 2200 is removed through line 3400 and it contains primarily butene-1 and isobutene. This product then is contacted with methanol from line 3800 in MTBE unit 3600 under conditions effective for reacting isobutene with methanol to form methyl tertiary butyl ether. Isobutene is selectively reactive with methanol and can be reacted to completion which upon separation of the reaction product leaves in line 4000 a butene-1 stream of high purity, e.g., greater than 99% by volume and produces a valuable by product methyl tertiary butyl ether in line 3900.

Figure 3:
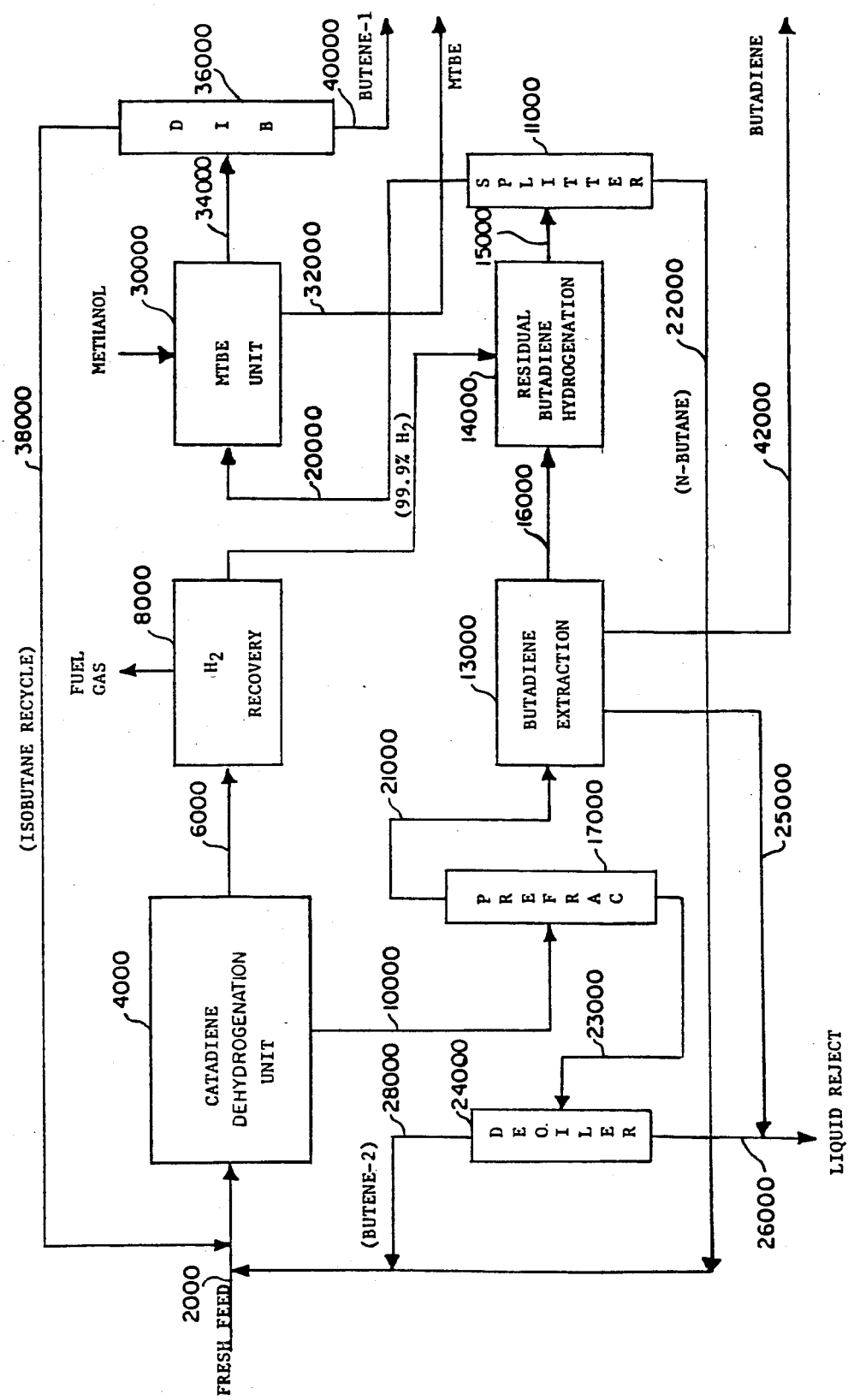
FIG. 3 is a process flow diagram showing production of butene-1 from n-butane with butadiene extraction.

The embodiment shown in FIG. 3 differs from the embodiment shown in FIG. 2 and FIG. 1, primarily because of the extraction of butadiene as a product rather than conversion of butadiene to monolefins and subsequent conversion to methyl tertiary butyl ether and butene-1. Better understanding is made by reviewing the process flow diagram in FIG. 3. As in the process described in FIG. 1, fresh feed containing n-butane is charged through line 2000 to a dehydrogenation unit 4000 with the lights being removed through line 6000 to hydrogen recovery unit 8000. The $C_4$ product from the unit is removed through line 10,000 from the dehydrogenation unit 400 to a prefractional column 17,000, where the butadiene and butene-1 are concentrated in the overhead and removed through line 21,000. The bottoms consisting of n-butane and butene-2 are passed via line 23,000 to deoiler 24,000 for fractionation and then the overhead recycled via line 28,000 to dehydrogenation unit 4000. The butadiene/butene-1 stream, which contains isobutane, isobutene, n-butane and butene-2 is sent to butadiene extraction unit 13,000 wherein it is contacted with a suitable solvent for recovering butadiene in high purity. Solvents which are selective for butadiene extraction can be used. An example is dimethylformamide. The raffinate stream 16,000 leaving butadiene extraction unit 13,000 is sent to a selective hydrogenation unit 14,000 where residual butadiene is converted to n-butane and butenes with minimum isomerization of butene-1 to butene-2. The product from the butadiene hydrogenation unit 14,000 is removed via line 15,000 to a splitter 11,000. The overheads containing isobutane, isobutylene and butene-1 is sent via line 20,000 to a methyl tertiary butyl ether unit 30,000 wherein it is contacted with methanol. Raffinate product from the MTBE unit 30,000 is removed via line 34,000 to a fractionation column 36,000 wherein isobutane is removed as an overhead via line 38,000 and butene-1 removed via line 40,000 as a bottoms fraction. The methyl tertiary butyl ether product is removed via line 32,000 from the unit.

The bottoms from splitter 11,000 is removed via line 22,000 and contains some n-butane; it is recycled to the dehydrogenation unit 4,000 via fresh feed line 2,000. Rejects, i.e., hydrocarbons which are suited primarily for purposes of fuel are removed from the deoiler 24,000 via line 26,000 and butadiene extraction unit 13,000 via line 25,000.

The following examples are provided to illustrate preferred embodiments of the invention and are not intended to restrict the scope thereof.

EXAMPLE 1

The procedure described in FIG. 1 is essentially followed in this example wherein a feedstock containing 99% by weight n-butane and 1% by weight of isobutane, is dehydrogenated in an adiabatic, fixed bed reactor system operating at temperatures from about 900°–1250° F. at pressures from about 0.1 to two atmospheres absolute. The catalyst used in the fixed bed reactor is a chromia-alumina catalyst. The reaction product obtained from the dehydrogenation unit consists essentially of isobutane, isobutene, n-butane, butene-1, butene-2, and 1, 3-butadiene which is fed to a hydrogenation unit wherein butadiene is selectively hydrogenated to butene-1 and butene-2 with minimum conversion of the butene-1 to n-butane. Hydrogenation is carried out in liquid phase reaction utilizing a platinum or palladium component as a catalyst. Ambient temperature and pressures from about one to ten atmospheres absolute are utilized.

After hydrogenation the reaction product is sent to a conventional distillation column operating at pressures between one and ten atmospheres absolute, wherein the butene-1 is recovered as overhead product along with isobutane and isobutene. A bottoms fraction containing primarily n-butane, and butene-2 is fractionated again for rejection of any $C_5+$ material.

Isobutene is separated from butene-1 by converting the isobutene to methyl tertiary butyl ether. This is accomplished by charging the overhead from the distillation column to a reaction zone where it is reacted with methanol in the liquid phase over a synthetic resin catalyst at ambient temperature. Conversion of isobutene in the methyl tertiary butyl ether unit is controlled to meet preselected purity specifications for butene-1 product. Conventional distillation is used to separate the methyl tertiary butyl ether from butene-1 and isobutane and the raffinate stream is sent to a distillation column operating at pressures from about three to ten atmospheres absolute where high purity butene-1 is recovered as a bottom product and isobutane is recovered as an overhead and recycled to the the dehydrogenation unit.

Table 1 provides a material balance for a feed stream containing 99% n-butane and 1% isobutane by weight, and Table 2 provides a material balance for a feed stock containing 75% n-butane and about 25% isobutane by weight.

TABLE 1

BUTENE-1 FROM N—BUTANE
(99 WT % N—BUTANE FEED)

|  | line 2 Fresh Feed | Losses | Light Gas | Liquid Reject | line 32 MTBE[1] | line 40 Butene-1 |
|---|---|---|---|---|---|---|
| $H_2$ |  |  | 3.10 |  |  |  |
| $C_1$-$C_3$ |  |  | 20.35 |  |  |  |
| $iC_4$ | 1.00 |  | 0.01 |  |  |  |
| $iC_4=$ |  |  | 0.01 |  |  | 0.27 |
| $C_4=1$ |  |  | 0.90 | 0.02 |  | 61.31 |
| $nC_4$ | 99.00 |  | 0.85 | 0.58 |  | 0.22 |
| $C_4=2$ |  |  | 1.18 | 0.90 |  | 0.12 |
| BD |  |  | 0.66 |  |  |  |
| $C_5+$ |  |  |  | 1.12 |  |  |
| Loss |  | 7.86 |  |  |  |  |
| MTBE |  |  |  |  | 0.86 |  |
| MEOH |  |  |  |  | 0.02 |  |
|  | 100.0 | 7.86 | 27.06 | 2.62 | 0.88 | 61.92 |

[1]MEOH added to MTBE unit at 0.34 wt % of fresh feed.
This process shows the production of low levels of methyl tertiary butyl ether with high levels of high purity butene-1.

TABLE 2

BUTENE-1 FROM N—BUTANE

|  | line 2 Fresh Feed | Losses | Light Gas | Liquid Reject | line 32 MTBE[1] | line 40 Butene-1 |
|---|---|---|---|---|---|---|
| $H_2$ |  |  | 3.16 |  |  |  |
| $C_1$-$C_3$ |  |  | 17.56 |  |  |  |
| $iC_4$ | 25.0 |  | 0.17 |  |  | 0.01 |
| $iC_4=$ |  |  | 0.13 |  |  | 0.20 |
| $C_4=1$ |  |  | 0.68 | 0.01 |  | 46.45 |
| $nC_4$ | 75.0 |  | 0.64 | 0.44 |  | 0.16 |
| $C_4=2$ |  |  | 0.89 | 0.68 |  | 0.10 |

TABLE 2-continued

BUTENE-1 FROM N—BUTANE

|  | line 2 Fresh Feed | Losses | Light Gas | Liquid Reject | line 32 MTBE[1] | line 40 Butene-1 |
|---|---|---|---|---|---|---|
| BD |  |  | 0.50 |  |  |  |
| $C_5+$ |  |  |  | 0.96 |  |  |
| Loss |  | 6.50 |  |  |  |  |
| MTBE |  |  |  |  | 32.62 |  |
| MEOH |  |  |  |  | 0.84 |  |
|  | 100.00 | 6.50 | 23.73 | 2.09 | 33.46 | 46.92 |

[1]MEOH added to MTBE unit at 12.70 wt % of fresh feed.
This process shows the production of high levels of methyl tertiary butyl ether with lower levels of butene-1 than the FIG. 1 embodiment but at the same high purity.

EXAMPLE 2

The procedure described in FIG. 2 is described as follows. As in Example 1 a feedstock containing a predominant portion of n-butane was dehydrogenated and any butadiene therein hydrogenated to produce butene-1, butene-2, and so forth. At this point the process differs from Example 1 in that the reaction product from the butadiene hydrogenation is sent to a deoiler tower for rejection of any heavy hydrocarbons such as $C_5+$, i.e., pentane, hexane, etc., and then to an extractive distillation unit where it is contacted with a solvent suited for separating the saturated hydrocarbon from the olefins. Dimethylformamide is an example of a solvent suited for such separation. The butene-1 containing fraction is sent to an ether producing unit wherein as in Example 1, the butene-1 is separated from isobutene therein, by catalytically reacting the isobutene to completion with methanol. Methyl tertiary butyl ether is produced as a product leaving butene-1 as an alternate product in high purity, e.g. greater than 99% per volume; the butadiene content in the butene-1 is less than about 100 ppm by weight. Yields are essentially the same as in Example 1.

EXAMPLE 3

The procedure described in FIG. 1 is followed except that suitable recovery facilities are provided to the scheme of FIG. 1, to produce high purity butadiene in conjunction with butene-1. This is shown in FIG. 3. Here, the product from unit 4000 is sent to a fractionator 17,000 where butadiene and butene-1 are concentrated in the overhead. The bottoms consisting of n-butane and butene-2 are recycled to the dehydrogenation unit 4000 via a deoiler tower 24,000 for rejection of $C_5+$ material. The butadiene/butene-1 stream which also will contain isobutane, isobutene, n-butane and butene-2 is then sent to an extractive distillation unit 13,000 where by use of a suitable solvent (DMF for example), high purity butadiene is recovered as a product. The raffinate stream is then sent to a selective hydrogenation unit 14,000 where residual butadiene is converted to n-butane and butenes with minimum isomerization of butene-1 to butene-2. The high purity butene-1 is then recovered by fractionation and conversion of isobutene to MTBE as described previously.

If extractive distillation is also used for recovery of butene-1 as described previously, it is possible to isolate the residual butadiene and recycle it to the butadiene extraction unit. This would eliminate the need for the selective hydrogenation step when butadiene is a co-product with butene-1. Table 3 presents yields for an operation of this type.

TABLE 3

BUTENE-1 AND BUTADIENE FROM N—BUTANE
(99 WT % N—BUTANE FEED)

| | line 200 Fresh Feed | Losses | Light Gas | Liquid Reject | Butadiene | line 3300 MTBE[1] | line 4000 Butene-1 |
|---|---|---|---|---|---|---|---|
| $H_2$ | | | 4.09 | | | | |
| $C_1$-$C_3$ | | | 20.02 | | | | |
| $iC_4$ | 1.00 | | 0.01 | | | | |
| $iC_4$=1 | | | 0.01 | | | | 0.13 |
| $C_4$=1 | | | 0.67 | | | | 31.47 |
| $nC_4$ | 99.00 | | 0.63 | 0.59 | | | 0.16 |
| $C_4$=2 | | | 0.88 | 0.31 | 0.34 | | 0.03 |
| BD | | | 0.42 | 0.41 | 33.31 | | |
| $C_5$+ | | | | 0.83 | | | |
| Loss | | 5.00 | | | | | |
| MTBE | | | | | | 1.09 | |
| MEOH | | | | | | 0.03 | |
| | 100.00 | 5.00 | 26.73 | 2.14 | 33.65 | 1.12 | 31.79 |

[1]MEOH added to MTBE unit at 0.43 wt % of fresh feed.
This process shows the production of high purity butadiene as a product in combination with high purity butene-1 and modest levels of methyl tertiary butyl ether.

What is Claimed is:

1. A process for producing high purity butene-1 from an n-butane containing feedstock which comprises the steps:
   (a) dehydrogenating a feed stock containing n-butane in the presence of a chromia-alumina catalyst thereby producing a reaction product containing butene-1, butene-2, isobutene, butadiene and by product heavies;
   (b) hydrogenating the butadiene product produced to produce additional butene-1 and butene-2;
   (c) fractionating the reaction product from the butadiene hydrogenation step to produce an overhead stream comprising butene-1 and isobutene and a bottoms fraction comprising n-butane, butene-2 and any other heavies;
   (d) reacting the overhead fraction from step (c) containing isobutene and butene-1 with methanol to form methyl tertiary butyl ether;
   (e) fractionating the methyl tertiary butyl ether from the reaction product in step (d) to produce a bottoms comprising methyl tertiary butyl ether and an overhead fraction comprising butene-1 and isobutane;
   (f) separating the isobutane from the butene-1 and recycling the isobutane to dehydrogenation zone described in step (a).

2. The process of claim 1 wherein the feedstock comprises from about 60 to 100% n-butane and the balance comprising $C_3$ to $C_5$ hydrocarbon.

3. A process for producing butene-1 and butadiene from a feedstock containing n-butane which comprises the steps:
   (a) dehydrogenating a feedstock containing n-butane in the presence of a chromia-alumina catalyst to produce a reaction product containing butene-1, butene-2, butadiene, and unreacted material;
   (b) distilling the reaction product from step (a) in a distillation column separating butene-2 from butadiene and butene-1, the butene-2, being removed as a bottoms fraction and the butene-1 and butadiene as an overheads fraction;
   (c) treating the bottoms fraction from the distillation column in a deoiler thereby removing butene-2 as an overhead fraction and any $C_5$ plus material as a bottoms fraction;
   (d) separating the overhead fraction from the distillation column by contacting with a solvent selective for butadiene into a high purity butadiene product and a raffinate stream containing butene-1, isobutane, isobutene and a small portion of residual butadiene;
   (e) passing the raffinate stream from the butadiene extraction through a hydrogenation zone thereby hydrogenating residual butadiene to form butene-1 and butene-2;
   (f) fractionating the reaction product from the hydrogenation in step (e) generating an overhead containing butene-1, isobutane and isobutene;
   (g) contacting the isobutene and butene-1 in the overhead from step (f) with methanol in a methyl tertiary butyl ether unit thereby forming methyl tertiary butyl ether;
   (h) fractionating the reaction product from the methyl tertiary butyl ether unit separating methyl tertiary butyl ether from the reaction product; and
   (i) fractionating the overhead fraction containing butene-1 and isobutane thereby producing an overhead containing isobutane for recycle to the dehydrogenation zone and a high purity butene-1 as a bottoms fraction.

4. A process for producing butene-1 from a feedstock containing n-butane and other $C_2$ to $C_6$ hydrocarbons which comprises the steps:
   (a) dehydrogenating a feedstock containing n-butane in the presence of a chromia-alumina catalyst to produce reaction product containing butene-1, butene-2, butadiene, and unreacted materials;
   (b) hydrogenating the butadiene product produced in the dehydrogenation step to produce additional butene-1 and butene-2;
   (c) fractionating the reaction product from the butadiene hydrogenation step to produce an overhead stream comprising butene-1, butene-2, and isobutene and a bottoms fraction containing $C_5$ plus hydrocarbons;
   (d) contacting the overhead stream from the fractionation of step (c) with a solvent selective for extracting butene-1 from butene-2 and saturated hydrocarbons;
   (e) separating the butene-2 from the saturates by fractionation;
   (f) isomerizing the butene-2 from the butene-1 extraction by contact with an isomerization catalyst and recycling the isomerization reaction product to the feed to the deoiler in step (c);

(g) contacting the butene-1 from the extraction in step (d) with methanol to convert the isobutylene to methyl tertiary butyl ether thereby generating a reaction product containing said ether and unreacted butene-1;

(h) fractionating the methyl tertiary butyl ether from the reaction product in step (g) to produce a bottoms comprising methyl tertiary butyl ether and an overhead fraction comprising butene-1; and then (i) recovering said butene-1 and methyl tertiary butyl ether.

* * * * *